United States Patent [19]

Beppu et al.

[11] Patent Number: 5,130,235
[45] Date of Patent: Jul. 14, 1992

[54] DNA ENCODING POLYPEPTIDE HAVING NITRILE HYDRATASE ACTIVITY AND METHOD FOR PRODUCING AMIDES FROM NITRILES WITH TRANSFORMANT CONTAINING THE SAME

[75] Inventors: Teruhiko Beppu, Tokyo; Sueharu Horinouchi, Chiba; Osamu Ikehata, Osamu; Takakazu Endo, Kangawa, all of Japan

[73] Assignee: Nitto Chemical Industry Co., Ltd., Tokyo, Japan

[21] Appl. No.: 372,449

[22] Filed: Jun. 28, 1989

[30] Foreign Application Priority Data

Jul. 6, 1988 [JP] Japan .................................. 63-166878
Aug. 16, 1988 [JP] Japan .................................. 63-202779

[51] Int. Cl.$^5$ .................. C12P 21/00; C12P 19/34; C12P 13/02; C12N 15/00
[52] U.S. Cl. .................. 435/68.1; 435/129; 435/235.1; 435/320.1; 435/252.3; 435/252.33; 435/227; 435/91; 435/172.3; 536/27; 530/350; 935/19; 935/29; 935/41; 935/56; 935/61; 935/73; 935/72; 935/82
[58] Field of Search ............ 435/68.1, 129, 235, 435/320.1, 252.3, 227, 252.33, 235.1, 91, 172.3; 536/271; 530/350; 935/19, 29, 41, 56, 61, 73, 72, 82

[56] References Cited

PUBLICATIONS

Ikehata et al., Eur. J. Biochem vol. 181 pp. 563–570 (1989).

*Primary Examiner*—Joan Ellis
*Attorney, Agent, or Firm*—Nixon & Vanderhye

[57] ABSTRACT

A DNA which encodes polypeptide carrying two specific amino acid sequences and having nitrile hydratase activity; a method for producing nitrile hydratase by incubating a transformant made by the transformation with a recombinant DNA prepared by integrating the foregoing DNA into a vector in a medium and harvesting nitrile hydratase accumulated in the medium; and a method for producing amides by incubating the foregoing transformant and then converting nitriles into corresponding amides by the action of the obtained nitrile hydratase or by making a culture solution, isolates, treated cells or their immobilized products act upon nitriles to produce corresponding amides.

12 Claims, 7 Drawing Sheets

FIG. 1

(1) AMINO ACID SEQUENCE

SUBUNIT α

α₁ : SerVal<u>ThrIleAspHisThrThrGluAsn</u>AlaAlaPro

α₂ : <u>ThrPheGluGluAspPhe</u>SerProArgArgGlyAlaGlu

SUBUNIT β

β₁ : <u>MetAspGlyValHisAsp</u>LeuAlaGlyValGlnGlyPhe

β₂ : ValProHisThrValAsnAlaAspIleGlyPro<u>ThrPhe</u>
<u>HisAlaGluTrpGluHisLeu</u>ProTyrSerLeuMet (2) DNA SEQUENCE OF PROBE

PROBE α1

3' TGG TAG CTG GTG TGG TGG CTT TT 5'

PROBE α2

5' ACN TTT GAA GAA GAC TT 3'
     C      G   G

PROBE β1

5' ATG GAT GGN GTA CAT GA 3'
          C         G   C

PROBE β2

3' TGG AAG GTG CGN CTT ACC CTT GTG GA 5'
             A         C         C (IN ABOVE FORMULAE, N IS A, T, G OR C.)

FIG. 3A

```
SphI
GCATGCTTTCCACATCTGGAACGTGATCGCCACGGACGGTGGTG
    .50
CCTACCAGATGTTGGACGGCAACGGATACGGCATGAACGCCAAG
              .100
GTTTGTACGATCCGGAACTGATGGCACACTTTGCTTCTCGACGCA
              .150
TTCAGCACGCCGACGCTCTGTCCGAAACCGTCAACTGGTGGCCC
              .200
TGACCGGCCACCACGGCATCACCACCCTCGGCGGCGCGAGCTACG
              .250
GCAAAGCCCGGAACCTCGTACCGCTTGCCCGCGCCGCCTACGACA
              .300
CTGCCTTGAGACAATTCGACGTCCTGGTGATGCCAACGCTGCCCT
              .350
ACGTCGCATCCGAATTGCCGGCGAAGGACGTAGATCGTGCAACCT
              .400
TCATCACCAAGGCTCTCGGGATGATCGCCAACACGGCACCATTCG
ACGTGACCGGACATCCGTCCCTGTCCGTTCCGGCCGGCCTGGTGA
.450
ACGGGGTTCCGGTCGGAATGATGATCACCGGCAGACACTTCGACG
    .500                                HindIII
ATGCGACAGTCCTTCGTGTCGGACGCGCATTCGAAAAGCTTCGCG
        .550
GCGCGTTTCCGACGCCGGCCGAACGCGCCTCCAACTCTGCACCAC
            .600
AACTCAGCCCCGCCTAGTCCTGACGCACTGTCAGACAACAAATTC
              .650
CACCGATTCACACATGATCAGCCCACATAAGAAAAGGTGAACCAG
              .700
ATGTCAGTAACGATCGACCACACAACGGAGAACGCCGCACCGGCC
        SerValThrIleAspHisThrThrGluAsnAlaAlaProAla
    Subunit α      Probe α₁      .750
CAGGCGGCGGTCTCCGACCGGGCGTGGGCACTGTTCCGCGCACTC
GlnAlaAlaValSerAspArgAlaTrpAlaLeuPheArgAlaLeu
```

FIG. 3B

```
              Kpn I                        . 800
GACGGTAAGGGATTGGTACCCGACGGTTACGTCGAGGGATGGAAG
AspGlyLysGlyLeuValProAspGlyTyrValGluGlyTrpLys
    .         .         .         .     . 850
AAGACCTTCGAGGAGGACTTCAGTCCAAGGCGCGGAGCGGAATTG
LysThrPheGluGluAspPheSerProArgArgGlyAlaGluLeu
         Probe α₂             .      Pvu II
GTAGCGCGCGCATGGACCGACCCCGAGTTCCGGCAGCTGCTTCTC
ValAlaArgAlaTrpThrAspProGluPheArgGlnLeuLeuLeu
. 900    Kpn I        .         .         .
ACCGACGGTACCGCCGCAGTTGCCCAGTACGGATACCTGGGCCCC
ThrAspGlyThrAlaAlaValAlaGlnTyrGlyTyrLeuGlyPro
      . 950       .         .         .
CAGGGCGAATACATCGTGGCAGTCGAAGACACCCCGACACTCAAG
GlnGlyGluTyrIleValAlaValGluAspThrProThrLeuLys
    .        . 1000      .         .
AACGTGATCGTGTGCTCGCTGTGTTCATGCACCGCGTGGCCCATC
AsnValIleValCysSerLeuCysSerCysThrAlaTrpProIle
    .         .       . 1050       .
CTCGGTCTGCCACCCACCTGGTACAAGAGCTTCGAATACCGTGCG
LeuGlyLeuProProThrTrpTyrLysSerPheGluTyrArgAla
    .         .         . 1100       .
CGCGTGGTCCGCGAACCACGGAAGGTTCTCTCCGAGATGGGAACC
ArgValValArgGluProArgLysValLeuSerGluMetGlyThr
    .         .         . 1150       .
GAGATCGCGTCGGACATCGAGATTCGCGTCTACGACACCACCGCC
GluIleAlaSerAspIleGluIleArgValTyrAspThrThrAla
    .         .         .     . 1200       .
GAAACTCGCTACATGGTCCTCCCGCAGCGTCCCGCCGGCACCGAA
GluThrArgTyrMetValLeuProGlnArgProAlaGlyThrGlu
    .        .   Pst I    .     . 1250
GGCTGGAGCCAGGAACAACTGCAGGAAATCGTCACCAAGGACTGC
GlyTrpSerGlnGluGlnLeuGlnGluIleValThrLysAspCys
    .         .         .         . 1300
CTGATCGGGGTTGCAATCCCGCAGGTTCCCACCGTCTGATCACCC
LeuIleGlyValAlaIleProGlnValProThrValTRM
              .      Subunit β      .
CGACAAGAAGGAAGCACACC-ATGGATGGAGTACACGATCTTGCC
                     MetAspGlyValHisAspLeuAla
                         Probe β₁
```

FIG. 3C

```
         .1350           .            .            .            .
GGAGTACAAGGCTTCGGCAAAGTCCCGCATACCGTCAACGCCGAC
GlyValGlnGlyPheGlyLysValProHisThrValAsnAlaAsp
         .1400           .            .            .            .
ATCGGCCCCACCTTTCACGCCGAATGGGAACACCTGCCCTACAGC
IleGlyProThrPheHisAlaGluTrpGluHisLeuProTyrSer
                .1450   Probe β₂      .                   Sal I
CTGATGTTCGCCGGTGTCGCCGAACTCGGGGCCTTCAGCGTCGAC
LeuMetPheAlaGlyValAlaGluLeuGlyAlaPheSerValAsp
         .               .1500        .            .
GAAGTGCGATACGTCGTCGAGCGGATGGAGCCGCGCCACTACATG
GluValArgTyrValValGluArgMetGluProArgHisTyrMet
         .               .            .1550        .
ATGACCCCGTACTACGAGAGGTACGTCATCGGTGTCGCGACATTG
MetThrProTyrTyrGluArgTyrValIleGlyValAlaThrLeu
         .               .            .1600        .
ATGGTCGAAAAGGGAATCCTGACGCAGGACGAACTCGAAAGCCTT
MetValGluLysGlyIleLeuThrGlnAspGluLeuGluSerLeu
         .               .            .1650        .
GCGGGGGGACCGTTCCCACTGTCACGGCCCAGCGAATCCGAAGGG
AlaGlyGlyProPheProLeuSerArgProSerGluSerGluGly
         .               .            .            .1700
CGGCCGGCACCCGTCGAGACGACCACCTTCGAAGTCGGGCAGCGA
ArgProAlaProValGluThrThrThrPheGluValGlyGlnArg
         .               .            .            .1750
GTACGCGTACGCGACGAGTACGTTCCGGGGCATATTCGAATGCCT
ValArgValArgAspGluTyrValProGlyHisIleArgMetPro
         .               .            .            .
GCATACTGCCGTGGACGAGTGGGAACCATCTCTCATCGAACTACC
AlaTyrCysArgGlyArgValGlyThrIleSerHisArgThrThr
  .1800                  .            .            .
GAGAAGTGGCCGTTTCCCGACGCAATCGGCCACGGGCGCAACGAC
GluLysTrpProPheProAspAlaIleGlyHisGlyArgAsnAsp
         .1850           .            .            .
GCCGGCGAAGAACCGACGTACCACGTGAAGTTCGCCGCCGAGGAA
AlaGlyGluGluProThrTyrHisValLysPheAlaAlaGluGlu
         .               .1900        .                   Sal I
TTGTTCGGTAGCGACACCGACGGTGGAAGCGTCGTTGTCGACCTC
LeuPheGlySerAspThrAspGlyGlySerValValValAspLeu
```

FIG. 3D

```
              .1950              .                   .
TTCGAGGGTTACCTCGAGCCTGCGGCCTGATCTTCCAGCATTCCA
PheGluGlyTyrLeuGluProAlaAlaTRM
                              .2000              .                   .
GGCGGCGGTCACGCGATCACAGCGGTTCGTGCGACCGCCGCCTGA
       .                      .        .2050     .                   .
TCACCACGATTCACTCATTCGGAAGGACACTGGAAATCATGGTCG
Sal I
AC
```

DNA ENCODING POLYPEPTIDE HAVING NITRILE HYDRATASE ACTIVITY AND METHOD FOR PRODUCING AMIDES FROM NITRILES WITH TRANSFORMANT CONTAINING THE SAME

BACKGROUND OF THE INVENTION

This invention relates to Rhodococcus sp. N-774-derived DNA encoding nitrile hydratase-active polypeptide having an ability of converting nitriles into corresponding amides and a method for producing amides from nitriles with a transformant containing the same.

An enzyme hydrating nitriles to form corresponding amides is known as nitrilase or nitrile hydratase. As examples of microorganisms producing the enzyme, microorganisms belonging to the genera Bacillus, Bacteridium, Micrococcus and Brevibacterium (see U.S. Pat. No. 4,001,081), Corynebacterium and Nocardia (see U.S. Pat. No. 4,248,968), Pseudomonas (see U.S. Pat. No. 4,637,982) and Rhodococcus, Arthrobacter and Microbacterium (see European Unexamined patent Application Publication No. 0188316), etc. can be enumerated.

SUMMARY OF THE INVENTION

In the hydration of nitriles with a nitrile hydratase gene prepared by the cloning according to genetic engineering, many copies of the nitrile hydratase gene can be made to exist in a microorganism. Consequently, it can be expected that the catalytic ability of a microorganism is increased by leaps and bounds a compared with the conventional methods.

Therefore, the present inventors made intensive researches into it, where they made their efforts to take out a DNA sequence encoding polypeptide having nitrile hydratase from a microorganism belonging to the genus Rhodococcus, make a recombinant DNA by integrating the DNA sequence into a vector, transform a microorganism with the recombinant DNA to make a transformant having higher nitrile hydratase activity and produce amides efficiently by using the transformant. Whereby, they have accomplished the present invention.

That is, an object of the present invention lies in providing a DNA encoding polypeptide having nitrile hydratase activity.

Another object of the present invention lies in providing a method for producing amides from nitriles by using a transformant containing a DNA encoding polypeptide having nitrile hydratase activity.

According to the present invention, a DNA sequence encoding polypeptide carrying specific amino acid sequences of Subunits α and β, which will be described later and having nitrile hydratase activity is defined and an expression plasmid containing this DNA and a transformant made by the transformation with the expression plasmid is obtained. In addition, nitrile hydratase can be produced by culturing this transformant and, furthermore, amides can be produced by making the transformant act upon nitriles.

BRIEF DESCRIPTION OF THE DRAWINGS

FIG. 1 (1) shows the results of amino acid sequencing in DNA probe making and the amino acid sequences (underlined part) used in probe synthesis.

FIG. 1 (2) shows DNA sequences of the probes.

FIG. 3 shows DNA sequence of N-774-derived DNA fragment contained in the recombinant plasmid pYUK121 and an amino acid sequence to be expected therefrom.

DETAILED DESCRIPTION OF THE INVENTION

Figure 2:
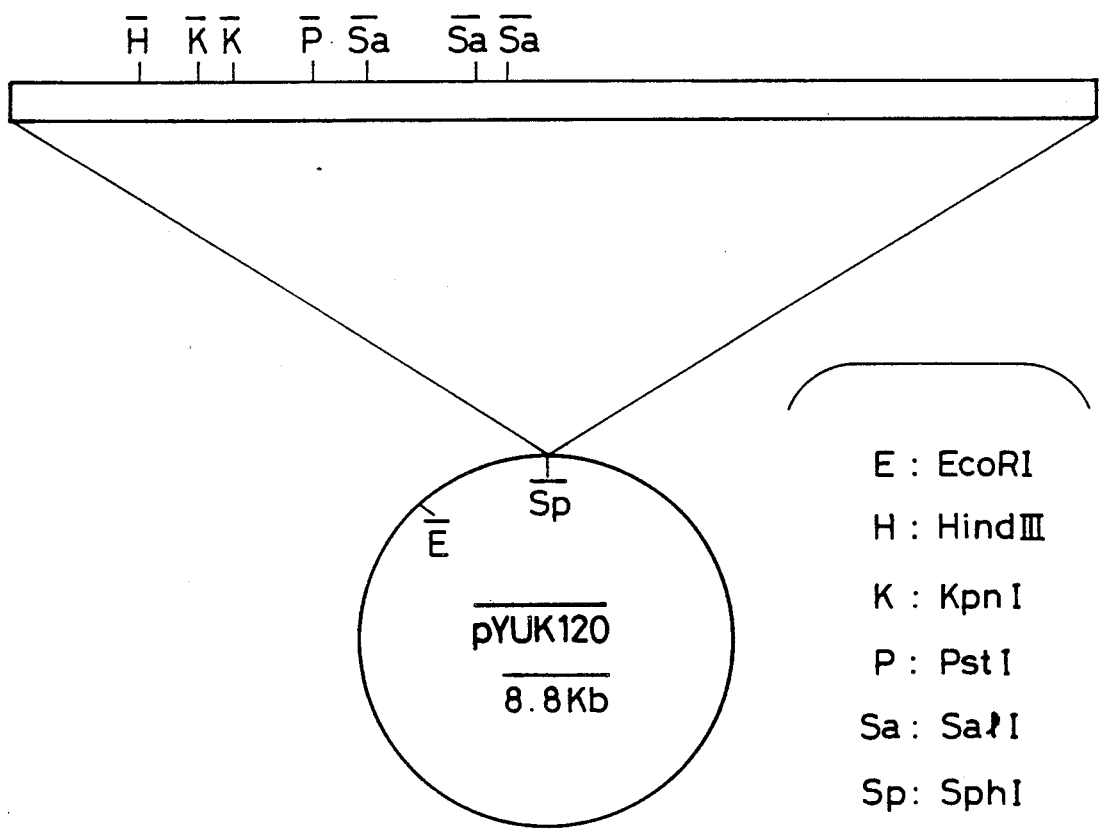
FIG. 2 shows a restriction endonuclease map of recombinant plasmid pYUK120.

As mentioned previously, this invention contemplates the provision of:

(1) a DNA encoding polypeptide carrying the following amino acid sequences of Subunits α and β and having nitrile hydratase activity:

Subunit α
```
            5                  10                 15
SerValThrIleAspHisThrThrGluAsnAlaAlaProAlaGln
            20                 25                 30
AlaAlaValSerAspArgAlaTrpAlaLeuPheArgAlaLeuAsp
            35                 40                 45
GlyLysGlyLeuValProAspGlyTyrValGluGlyTrpLysLys
            50                 55                 60
ThrPheGluGluAspPheSerProArgArgGlyAlaGluLeuVal
            65                 70                 75
AlaArgAlaTrpThrAspProGluPheArgGlnLeuLeuLeuThr
            80                 85                 90
AspGlyThrAlaAlaValAlaGlnTyrGlyTyrLeuGlyProGln
            95                 100                105
GlyGluTyrIleValAlaValGluAspThrProThrLeuLysAsn
            110                115                120
ValIleValCysSerLeuCysSerCysThrAlaTrpProIleLeu
            125                130                135
GlyLeuProProThrTrpTyrLysSerPheGluTyrArgAlaArg
            140                145                150
ValValArgGluProArgLysValLeuSerGluMetGlyThrGlu
            155                160                165
IleAlaSerAspIleGluIleArgValTyrAspThrThrAlaGlu
            170                175                180
ThrArgTyrMetValLeuProGlnArgProAlaGlyThrGluGly
            185                190                195
TrpSerGlnGluGlnLeuGlnGluIleValThrLysAspCysLeu
            200                205
IleGlyValAlaIleProGlnValProThrVal
```

Subunit β
```
            5                  10                 15
MetAspGlyValHisAspLeuAlaGlyValGlnGlyPheGlyLys
            20                 25                 30
ValProHisThrValAsnAlaAspIleGlyProThrPheHisAla
            35                 40                 45
GluTrpGluHisLeuProTyrSerLeuMetPheAlaGlyValAla
            50                 55                 60
GluLeuGlyAlaPheSerValAspGluValArgTyrValValGlu
            65                 70                 75
ArgMetGluProArgHisTyrMetMetThrProTyrTyrGluArg
            80                 85                 90
TyrValIleGlyValAlaThrLeuMetValGluLysGlyIleLeu
            95                 100                105
ThrGlnAspGluLeuGluSerLeuAlaGlyGlyProPheProLeu
            110                115                120
SerArgProSerGluSerGluGlyArgProAlaProValGluThr
            125                130                135
ThrThrPheGluValGlyGlnArgValArgValArgAspGluTyr
            140                145                150
ValProGlyHisIleArgMetProAlaTyrCysArgGlyArgVal
            155                160                165
GlyThrIleSerHisArgThrThrGluLysTrpProPheProAsp
            170                175                180
AlaIleGlyHisGlyArgAsnAspAlaGlyGluGluProThrTyr
            185                190                195
HisValLysPheAlaAlaGluGluLeuPheGlySerAspThrAsp
            200                205                210
GlyGlySerValValValAspLeuPheGluGlyTyrLeuGluPro
AlaAla,
```

(2) A DNA of the above (1) whose DNA sequences encoding Subunits α and β are respectively as follows:

Subunit α

```
         10        20        30        40
    TCAGTAACGATCGACCACACAACGGAGAACGCCGCACCGG
         50        60        70        80
    CCCAGGCGGCGGTCTCCGACCGGGCGTGGGCACTGTTCCG
         90       100       110       120
    CGCACTCGACGGTAAGGGATTGGTACCCGACGGTTACGTC
        130       140       150       160
    GAGGGATGGAAGAAGACCTTCGAGGAGGACTTCAGTCCAA
        170       180       190       200
    GGCGCGGAGCGGAATTGGTAGCGCGCGCATGGACCGACCC
        210       220       230       240
    CGAGTTCCGGCAGCTGCTTCTCACCGACGGTACCGCCGCA
        250       260       270       280
    GTTGCCCAGTACGGATACCTGGGCCCCCAGGGCGAATACA
        290       300       310       320
    TCGTGGCAGTCGAAGACACCCCGACACTCAAGAACGTGAT
        330       340       350       360
    CGTGTGCTCGCTGTGTTCATGCACCGCGTGGCCCATCCTC
        370       380       390       400
    GGTCTGCCACCCACCTGGTACAAGAGCTTCGAATACCGTG
        410       420       430       440
    CGCGCGTGGTCCGCGAACCACGGAAGGTTCTCTCCGAGAT
        450       460       470       480
    GGGAACCGAGATCGCGTCGGACATCGAGATTCGCGTCTAC
        490       500       510       520
    GACACCACCGCCGAAACTCGCTACATGGTCCTCCCGCAGC
        530       540       550       560
    GTCCCGCCGGCACCGAAGGCTGGAGCCAGGAACAACTGCA
        570       580       590       600
    GGAAATCGTCACCAAGGACTGCCTGATCGGGGTTGCAATC
        610
    CCGCAGGTTCCCACCGTC
```

Subunit β

```
         10        20        30        40
    ATGGATGGAGTACACGATCTTGCCGGAGTACAAGGCTTCG
         50        60        70        80
    GCAAAGTCCCGCATACCGTCAACGCCGACATCGGCCCCAC
         90       100       110       120
    CTTTCACGCCGAATGGGAACACCTGCCCTACAGCCTGATG
        130       140       150       160
    TTCGCCGGTGTCGCCGAACTCGGGGCCTTCAGCGTCGACG
        170       180       190       200
    AAGTGCGATACGTCGTCGAGCGGATGGAGCCGCGCCACTA
        210       220       230       240
    CATGATGACCCCGTACTACGAGAGGTACGTCATCGGTGTC
        250       260       270       280
    GCGACATTGATGGTCGAAAAGGGAATCCTGACGCAGGACG
        290       300       310       320
    AACTCGAAAGCCTTGCGGGGGGACCGTTCCCACTGTCACG
        330       340       350       360
    GCCCAGCGAATCCGAAGGGCGGCCGGCACCCGTCGAGACG
        370       380       390       400
    ACCACCTTCGAAGTCGGGCAGCGAGTACGCGTACGCGACG
        410       420       430       440
    AGTACGTTCCGGGGCATATTCGAATGCCTGCATACTGCCG
        450       460       470       480
    TGGACGAGTGGGAACCATCTCTCATCGAACTACCGAGAAG
        490       500       510       520
    TGGCCGTTTCCCGACGCAATCGGCCACGGGCGCAACGACG
        530       540       550       560
    CCGGCGAAGAACCGACGTACCACGTGAAGTTCGCCGCCGA
        570       580       590       600
    GGAATTGTTCGGTAGCGACACCGACGGTGGAAGCGTCGTT
        610       620       630
    GTCGACCTCTTCGAGGGTTACCTCGAGCCTGCGGCC,
```

(3) a recombinant DNA in which the DNA of the above (1) or (2) is integrated, (4) a transformant made by the transformation with a recombinant DNA of the above (3), (5) a method for producing nitrile hydratase by incubating the transformant of the above (4), (6) a method for producing amides from nitriles by incubating a transformant of the above (4) and then converting nitriles into amides by the action of nitrile hydratase to be obtained, and, (7) a method for manufacturing amides by incubating a transformant of the above (4) and then making a culture solution, isolates, treated cells or their immobilized products of the obtained transformant act upon nitriles to produce corresponding amides.

hereinafter, the present invention will be described in detail.

The present invention is carried out by going through the following Steps (1) to (8):

(1) Partial Determination of Amino Acid Sequence of Nitrile Hydratase and Making of DNA Probe thereby Nitrile hydratase is extracted and purified from the incubated and harvested Rhodococcus sp. N-774 and then separated into two subunits by high performance liquid chromatography. Then, a part of amino acid sequence of each subunit is determined, on the basis of which probes carrying DNA sequences to be expected from the amino acid sequences are made (FIG. 1).

(2) preparation of DNA Fragment Containing Nitrile Hydratase Gene

A chromosomal DNA is isolated from Rhodococcus sp. N-774. After digesting the isolated chromosomal DNA with a restriction enzyme, a DNA fragment containing the aimed gene is detected by suing probes of the above (1) according to Southern hydbridization technique [E. M. Southern, *J. Mol. Biol.* 98, 503 (1975); this note will be applied the same hereinafter].

(3) Insertion of Chromosomal DNA Fragment into Vector

A chromosomal DNA fragment prepared in Step (2) is inserted into a vector to make a recombinant DNA library.

(4) making of Transformant and Selection of Recombinant DNA

Transformants are made by using a recombinant DNA library prepared in step (3), from which a transformant containing the aimed recombinant DNA is selected by using probes made in Step (1) according to colony hydridization technique [R. Bruce Wallace et al, *Nuc. Aci. Res.* 9, 879 (1981); this note will be applied the same hereinafter]. then, the reconfirmation of the aimed recombinant DNA is carried out according to the Southern hydbridization technique. The recombinant DNA selected in this step is designated pYUK120.

(5) Purification of Recombinant DNA ad Construction of Restriction Endonuclease Map After purifying pYUK120 obtained in Step (4), a restriction endonuclease map (FIG. 2) is made to determine the location containing the aimed gene.

(6) Determination of DNA Sequence

From a chromosnal DNA fragment derived from a parent strain of pYUK120, unnecessary parts are removed by using a restriction enzyme. Then, all the DNA sequences of the obtained DNA fragment (FIG. 3) are determined to reconfirm that the DNA fragment contains the DNA sequence to be expected from the amino acid sequence determined in Step (1).

(7) Preparation of Expression Plasmid and Making of Transformant

Figure 4:
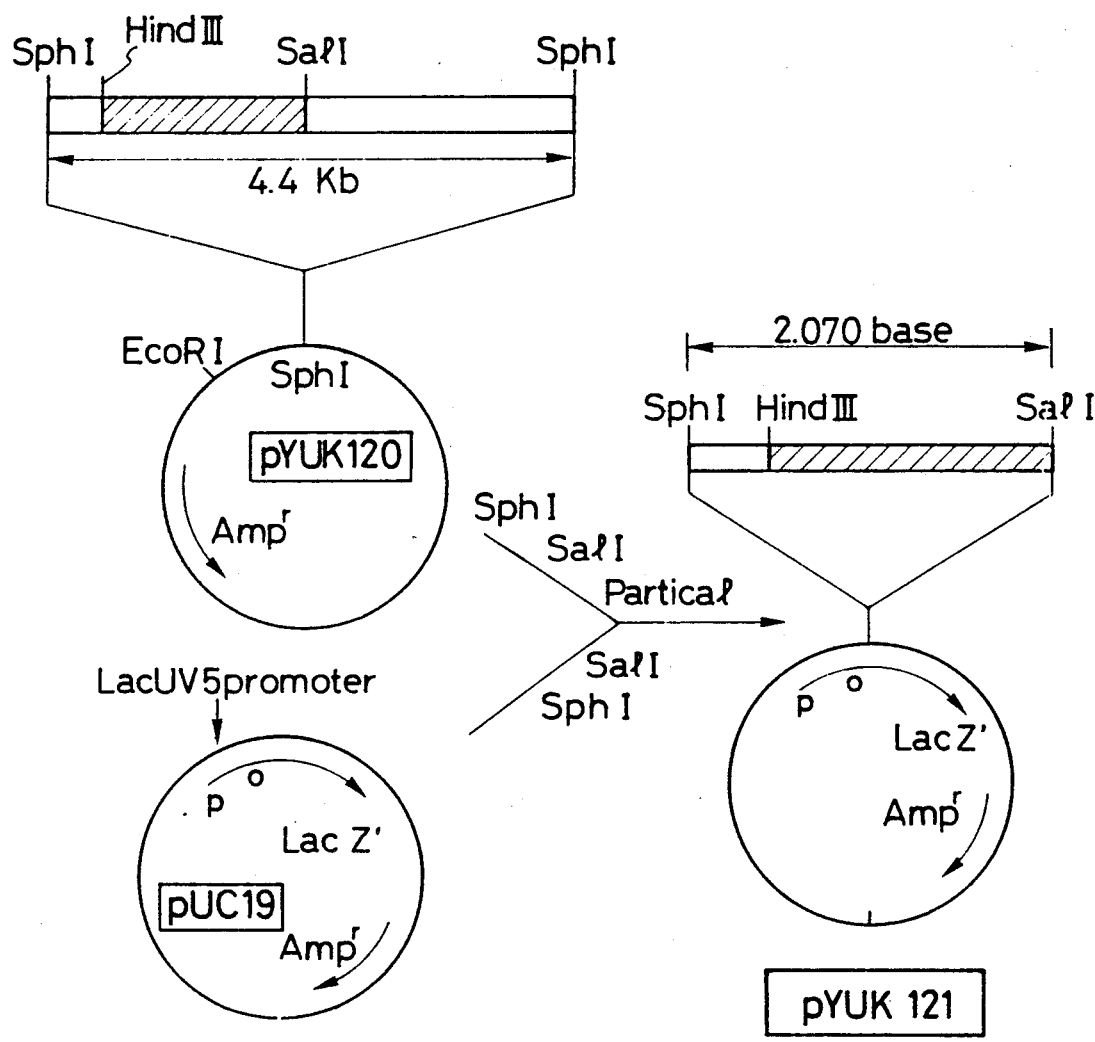
FIG. 4 shows a method for preparing the expression plasmid pYUK121.

The DNA fragment containing the aimed gene made in Step (6) is ligated to pUC19 (manufacture by Takara Shuzo Co., Ltd.) carrying a lac promoter on the downstream of the promoter to make an expression plasmid, which is designated pYUK121 (FIG. 4). This plasmid is transformed into *E. coli* 105 (manufactured by Amersham Inc.).

(8) Production of Nitrile Hydratase by Using Transformant and Conversion of Nitriles into Amides The transformant containing pYUK121 made in Step (6) is incubated. From the culture, a crude enzyme is prepared. This crude enzyme is mixed with a substrate solution containing nitriles to produce amides.

Incidentally, Rhodococcus sp. N-774 [this strain has been classified as a member of the genus Corynebacterium on the eighth edition (1974) of Bergy's *Manual of Determinative Bacteriology* and was deposited in Fermentation Research Institute with the accession number FERM-P No. 4446, see U.S. Pat. No. 4,248,968) and a transformant JM105l/pYUK121 made in Step (7) are deposited in Fermentation Research Institute respectively with accession numbers FERM BP-1936 and FERM BP-1937.

As a vector to be used in the above steps, any of plasmid vectors (for example, pACYC177, pSC101, etc.), phage vectors [for example, λgt11 (manufactured by Toyobo Co., Ltd.), Charon4A (manufactured by Amersham Inc.), etc.] will do. In addition, any controllable promoter other than lac can be used in the above steps. A host strain to be used for the transformation is not restricted to *E. coli* JM105 particularly.

In the conversion of nitriles into amides, not only purified enzymes but also a culture solution, isolates, treated cells, their immobilized products, etc. of a transformant can be used other than crude enzyme.

Nitriles are generally represented by the formula $R\text{-}(CN)_n$ and branched off in mononitrile ($n=1$) and polynitrile ($n \geq 2$) corresponding to the value of n. In addition, R in the formula is a hydrogen atom or a straight chain, branched chain or cyclic saturated or unsaturated hydrocarbon residue with various carbon numbers, a hydrocarbon residue having a substituent such as amino group, hydroxyl group, halogen group, carboxyl group or the like, so that a wide range of compounds are included.

As specific examples thereof, acetonitrile, propionitrile, n-butylonitrile, 1-butylonitrile, n-valeronitrile, acrylonitrile, methacrylonitrile, benzonitrile, cyanopyridine, malononitrile, succinonitrile, fumaronitrile, chloroacetonitrile, β-hydroxypropionitrile, aminoacetonitrile, β-aminopropionitrile, etc. can be enumerated.

Hereinafter, the present invention will be described, referring to an example.

In the example, the following abbreviations will be used.

TE: Tris-HCl (10 mM, pH 7.8), EDTA (1 mM, pH 8.0)

TNE: Tris-HCl (50 mM, pH 8.0), EDTA (1 mM, pH 8.0), NaCl (50 mM)

STE: Tris-HCl (50 mM, pH 8.0), EDTA (B 5 mM, pH 8.0), Sucrose (35 mM)

2XYT medium: 1.6% tryptone, 1.0% yeast extract, 0.5% NaCl

EXAMPLE (1) Partial Determination of Amino Acid Sequence of Nitrile Hydratase and Synthesis of DNA Probe thereby After incubating Rhodococcus sp. N-774 in a medium (glucose, 10 g/l; peptone, 5 g/l; yeast extract, 3 g/l; malt extract, 3 g/l; ferrous sulfate, 0.01 g/l; water, 1 l; pH 7.2) at 30° C. for 48 hours, cells were harvested. Then, the cells were pulverized, subjected to ammonium sulfate fractionation and dialyzed. The dialysate was centrifuged, and the supernatant was pipetted off and subjected to DEAE-cellulofine chromatography, phenyl-Sepharose chromatography, Sephdex G-150 chromatography and Octyl-Sepharose chromatography to obtain active fractions. The active fractions were then dialyzed to obtain an enzyme solution. The enzyme was separated into two subunits ($\alpha$ and $\beta$) by high performance liquid chromatography using a reversed phase column (Senshu Pak VP-304-1251 manufactured by Senshu Scientific Co., Ltd.) Amino acid sequences ($\alpha_1$ and $\beta_1$) from N-termini of the subunits and amino acid sequences ($\alpha_2$ and $\beta_2$) from N-termini of peptide fragment obtained by lysyl-endopeptidase digestion were determined by using an amino acid sequencer (470A manufactured by Applied Bio System, Inc.). Then, four kinds ($\alpha_1$, $\alpha_2$, $\beta_1$ and $\beta_2$) of probes having DNA sequences to be expected from the foregoing amino acid sequences were synthesized by using a DNA autosynthesizer (System 1 plus manufactured by Beckmann Instruments, Inc.).

The results of this amino acid sequencing, the amino acid sequences used for probe synthesis and the DNA sequences of the probes were shown in FIG. 1.

(2) Preparation of DNA Fragment Containing Nitrile Hydratase Gene

Rhodococcus sp. N-774 was inoculated and incubated on 100 ml of medium (prepared by adding 1% glycine or 0.2 µg/ml ampicillin to a MY medium), followed by harvesting cells. After washing with TNE, the cells were suspended in 10 ml of TE, whereto 4 ml of 0.25M EDTA, 10 to 20 mg of lysozyme, 10 to 20 mg of achromoprotease and 10 ml of 10% SDS were then added. The suspension was allowed to stand at 37° C. for 3 hours, followed by addition of 15 ml of phenol (60° C.). The resultant solution was allowed to stand at 60° C. for 15 minutes, followed by centrifugation. Then, the upper layer of the solution was collected, to which 0.7 ml of 2.5M sodium acetate solution and diethyl ether were then added. After centrifuging this solution, the upper layer of the resultant solution was discarded. Then, 2 volumes of ethanol was added to the remaining lower layer and DNA was spooled out therefrom with a glass rod. The obtained DNA was soaked successively in 2:8, 1:9 and 0.10 TE:ethanol solutions for each 5 minutes and then dissolved in 2 to 4 ml of TE (37° C.). To this solution, were added 10 µl of mixture of RNases A and $T_1$ at 37° C. and then an equal volume of phenol. After centrifuging the resultant solution, the upper layer was collected and an equal volume or more of ether was added thereto. Then, the resultant solution was centrifuged, the upper layer was discarded and the remaining lower layer was dialyzed overnight against 2 l of TE containing a small volume of chloroform. Then, the second dialysis was carried out for 3 to 4 hours to botain approx. 4 ml of crude chromosonal DNA preparation.

After making 15 µl of crude chromosonal DNA preparation react by adding 2 µl of restriction enzyme Sph I, 3 µl of restriction buffer for Sph I (10-fold concentration) and 10 µl of TE at 37° C. for 1 hour, the reaction solution was subjected to agarose gel electrophoresis (60V, 3 hours). Then, Southern hydrization was carried out by using DNA probes synthesized in Step (1). As the result, it was found that DNA fragments to which the above synthetic probes $\alpha_1$, $\alpha_2$, $\beta_2$ strongly hybridized located at approx. 4.4-Kb.

After digesting another 15 µl of crude chromosonal DNA with a restriction enzyme Sph I (manufactured by Takara Shuzo Co., Ltd.) in the same manner as aforementioned, the digested DNA was subjected to agarose gel electrophoresis and a gel containing 4.4-Kb DNA fragments was cut out. After solubilizing the gel by adding thereto 3-fold volumes of 8M NaClO$_4$ solution, DNA was adsorbed on a 6 mm diameter GF/C filter paper (manufactured by Whatman Corp.). To this DNA-adsorbed filter paper, were dropwise added 100 µl of TE containing 6M NaClO$_4$ and then 100 µl of 95% ethanol respectively 10 times. Thus treated filter paper was air-dried for 3 minutes and then placed in a 0.5-ml Eppendorf tube, followed by addition of 40 µl of TE. After standing at 37° C. for 30 minutes, the tube was centrifuged and then approx. 40 µl of its supernatant was separated. In this solution, 4.4-Kb DNA fragments containing the aimed nitrile hydratase chromosonal DNA was recovered.

(3) Insertion of Chromosonal DNA Fragment into Vector

To 10 µl of plasmid pBR322 (manufactured by Takara Shuzo Co., Ltd.), were added 2 µl of restriction enzyme Sph I, 3 µl of restriction buffer for Sph I (10-fold concentration) and 10 µl of TE. The resultant solution was incubated at 30° C. for 1 hour, followed by discontinuance of the reaction by adding thereto 2 µl of 0.25M EDTA. Then, 7 µl of 1M Tris-HCl (pH 9) and 3 µl of BAP (bacterial alkaline phosphatase) were added to the reaction solution and the resultant solution was incubated at 65° C. for 1 hours. Then, TE was added to the reaction solution to give a total volume of 100 µl and the resultant solution was extracted 3 times with an equal volume of phenol. Then, an equal volume of ether was added to the extract to collect the lower layer, followed by addition of 10 µl of 3M sodium acetate solution and 250 µl of ethanol to the layer. After standing at −80° C. for 30 minutes, the resultant solution was centrifuged. The pellet was dried and dissolved in TE.

5 µl of pBR322 digested with Sph I and treated with BAP as described above and 40 µl of 4.4-Kb DNA fragment solution recovered in Step (2) were mixed. Then, 6 µl of ligation buffer, 6 µl of 6 mg/ml ATP solution and 3 µl of T4-DNA ligase (manufactured by Takara Shuzo Co., Ltd.) were added to the mixture solution, followed by incubating overnight (12 hours) at 4° C. Whereby, approx. 60 µl of recombinant plasmid in which 4.4-Kb DNA fragments were inserted into pBR322 was made. The recombinant plasmid was considered as a DNA library.

(4) Making of Transformant and Selection of Recombinant DNA

E. coli TG1 (manufactured by Amersham Corp.) was inoculated into 10 ml of 2×YT medium at 37° C. After a 12-hour incubation, 1% portion of the culture was inoculated on a new 2×YT medium and incubated at 37° C. for 2 hours. After harvesting cells by centrifugation, 5 ml of cold 50 mM CaCl$_2$ solution was added to the cells. After standing at 0° C. for 40 minutes, the resultant cell solution was centrifuged again. Then, 0.25 ml of cold 50 mM CaCl$_2$ solution and 60 µl of recombinant plasmid solution prepared in Step (3) were added to the pellet. After standing at 0° C. for 40 minutes, the resultant solution was heat shocked at 42° C. for 2 minutes and allowed to stand again at 0° C. for 5 minutes. After adding 10 ml of 2×YT medium, the resultant solution was incubated at 37° C. for 90 minutes and then cells were harvested therefrom by centrifugation. After making the harvested cells suspend homogeneously in 1 ml of 2×YT medium, the suspension as dispensed in 10 µl portions into two agar plates of 50 µg/ml ampicillin-containing 2×YT medium and incubated at 37° C. From transformant colonies grown on the plate, transformants having nitrile hydratase gene were selected by colony hybridization technique. That is, transformants incubated in the plates were moved onto a nitrocellulose filter and cells thereof were lysed to immobilize DNA. Then, the immobilized DNA was treated with synthetic probes and colonies containing the aimed recombinant DNA were selected by autoradiography. From the selected colonies, recombinant plasmids were prepared and hybridized with all of four kinds of synthetic probes by Southern hybridization technique, thereby reconfirming that the selected colonies were transformants containing the aimed gene.

(5) Purification of Recombinant Plasmid and Making of Restriction Endonuclease Map Transformants selected in Step (4) were inoculated into 100 ml of 2×YT medium (containing 50 μg/ml ampicillin) and incubated overnight (12 hours) at 37° C. After harvesting cells, TNE was added thereto and the cells were harvested again. Then, 8 ml of STE and 10 mg of lysozyme were added to the cells and this solution was incubated at 0° C. for 5 minutes. After the completion of reaction, firstly 4 ml of 0.25M EDTA and then 2 ml of 10% SDS and 5 ml of 5M NaCl at room temperature were added to the reaction solution, followed by standing at 0° to 4° C. for 3 hours. The resultant solution was ultracentrifuged. After adding ½ equivalent of 30% PEG6000 to the supernatant, the resultant solution was allowed to stand overnight (12 hours) at 0° to 4° C. and then centrifuged again. The obtained pellet was dissolved in TNE to give a volume of 7.5 ml. After adding CsCl thereto, the resultant solution was centrifuged to remove protein. Then, 300 to 500 mg/ml ethidium bromide solution was added to the solution. The resultant solution was poured into a centrifuge tube, which was then sealed by heat and ultracentrifuged. Then, cccDNA was taken out by a peristaltic pump, and ethidium bromide was removed from the cccDNA by adding thereto an equal volume or more of water-saturated isopropyl alcohol. Thus treated cccDNA was dialyzed against TE to obtain approx. 3 ml of purified recombinant plasmid, which was designated pYUK120.

The obtained recombinant plasmid was digested with restriction enzymes such as EcoR I, Hind II, Knp I, Pst I, Sal I and Sph I (all manufactured by Takara Shuzo Co., Ltd.) and the like to make a restriction endonuclease map shown in FIG. 2.

(6) Determination of DNA Sequence

The location of the aimed gene in a DNA fragment derived from pYUK120 was determined by the restriction endonuclease map made in Step (5) and Southern hybridization technique. Then, unnecessary parts were cut out with restriction enzymes Sph I and Sal I to shorten the chain length from 4.4 Kb to 2.07 Kb. All the DNA sequences of thus obtained DNA fragment were determined according to Sanger method [F. Sanger, *Science* 214, 1205–1210 (1981)] using M13 phage vector. As the result, the DNA sequence of this 2.07-Kb DNA fragment derived from Rhodococcus sp. N-774 was found to be that shown in FIG. 3.

Incidentally, it was confirmed that this DNA sequence contained all of the DNA sequences expected from the amino acid sequence determined in Step (1) and it became clear that both of Subunits α and β existed in this DNA fragment.

(7) Preparation of Expression Plasmid and Making of Transformant 2.07-Kb DNA fragments made in Step (6) were ligated with plasmid pUC19 digested with restriction endonuclease Sph I and Sal I to make approx. 3 ml of expression plasmid designated pYUK121 (FIG. 4).

By the use of this plasmid pYUK121, a transformant JM105/pYUK121 (Accession No. FERM BP-1937) (whose hose was *E. coli* JM105) was made in the same manner as in Step (6).

(a) Production of Nitrile Hydratase by Using Transformant and Conversion of Nitriles into Amides

*E. coli* JM 105 containing pYUK121 was incubated overnight in 10 ml of 2×YT medium (containing 50 μg/ml ampicillin) at 30° C. Then, 1% portions of this culture were inoculated into 100 ml of 2×YT medium (containing 50 μg/ml ampicillin, 10 mg/l FeSO$_4$·7H$_2$O and pyrro-quinoline quinone) and incubated at 30° C. for 2 hours. After adding IPTG to give a final concentration of 2 mM, the resultant culture was further incubated at 30° C. for 15 hours.

After harvesting cells from the above culture, the cells were suspended in 3 ml of 1/20M phosphate buffer (containing 0.35% sodium n-lactate, pH 7.7). The suspension was subjected to sonication and then to centrifugation. The pellet was dissolved in 20 ml of the above phosphate buffer containing 8M urea, followed by adding thereto 0.585 g of sodium chloride. The resultant solution was adjusted to have a pH of 10.0, followed by dialyzing against 3 l of 50 mM Tris-HCl buffer (pH 7.7) for 3 hours. The dialysate was further dialyzed overnight against 3 l of 1/20M phosphate buffer (pH 7.7) to botain approx. 35 ml of crude enzyme.

2 ml of this crude enzyme was mixed with 2 ml of substrate solution (containing 5% acrylonitrile, 0.35% sodium n-lactate, 10 mg/l FeSO$_4$·7H$_2$O, 1 μg/l PQQ and 50 mM phosphate buffer; pH 7.7), followed by incubating at 20° C. for 20 minutes under light exposure. The reaction was stopped by adding 2 ml of 1N HCl. The reaction solution was subjected to high performance liquid chromatography to detect the formed acrylamide and the unreacted acylonitrile in it. As the result, acrylamide could not be detected in the crude extract from the host *E. coli* JM105, whereas it was detected in pYUK121-containing *E. coli* JM105 according to the present invention. The specific activity of acrylamide was 13.2U per liter of medium, where 1U meant μmol number of acrylamide to be formed in 1 minute.

What is claimed is:

1. An isolated and purified DNA sequence encoding a polypeptide selected from the group consisting of subunit α and subunit β, wherein said subunits possess nitrile hydratase activity and comprise the amino acid sequence as follows:

Subunit α

```
         5                 10                15
SerValThrIleAspHisThrThrGluAsnAlaAlaProAlaGln 20                25                30
AlaAlaValSerAspArgAlaTrpAlaLeuPheArgAlaLeuAsp 35                40                45
GlyLysGlyLeuValProAspGlyTyrValGluGlyTrpLysLys 50                55                60
ThrPheGluGluAspPheSerProArgArgGlyAlaGluLeuVal 65                70                75
AlaArgAlaTrpThrAspProGluPheArgGlnLeuLeuLeuThr 80                85                90
AspGlyThrAlaAlaValAlaGlnTyrGlyTyrLeuGlyProGln 95               100               105
GlyGluTyrIleValAlaValGluAspThrProThrLeuLysAsn 110               115               120
ValIleValCysSerLeuCysSerCysThrAlaTrpProIleLeu 125               130               135
GlyLeuProProThrTrpTyrLysSerPheGluTyrArgAlaArg
```

-continued 140 145 150
ValValArgGluProArgLysValLeuSerGluMetGlyThrGlu 155 150 165
IleAlaSerAspIleGluIleArgValTyrAspThrThrAlaGlu 170 175 180
ThrArgTyrMetValLeuProGlnArgProAlaGlyThrGluGly 185 190 195
TrpSerGlnGluGlnLeuGlnGluIleValThrLysAspCysLeu 200 205
IleGlyValAlaIleProGlnValProThrVal Subunit β

5 10 15
MetAspGlyValHisAspLeuAlaGlyValGlnGlyPheGlyLys 20 25 30
ValProHisThrValAsnAlaAspIleGlyProThrPheHisAla 35 40 45
GluTrpGluHisLeuProTyrSerLeuMetPheAlaGlyValAla 50 55 60
GluLeuGlyAlaPheSerValAspGluValArgTyrValValGlu 65 70 75
ArgMetGluProArgHisTyrMetMetThrProTyrTyrGluArg

-continued 80 85 90
TyrValIleGlyValAlaThrLeuMetValGluLysGlyIleLeu 95 100 105
ThrGlnAspGluLeuGluSerLeuAlaGlyGlyProPheProLeu 110 115 120
SerArgProSerGluSerGluGlyArgProAlaProValGluThr 125 130 135
ThrThrPheGluValGlyGlnArgValArgValArgAspGluTyr 140 145 150
ValProGlyHisIleArgMetProAlaTyrCysArgGlyArgVal 155 160 165
GlyThrIleSerHisArgThrThrGluLysTrpProPheProAsp 170 175 180
AlaIleGlyHisGlyArgAsnAspAlaGlyGluGluProThrTyr 185 190 195
HisValLysPheAlaAlaGluGluLeuPheGlySerAspThrAsp 200 205 210
GlyGlySerValValValAspLeuPheGluGlyTyrLeuGluPro AlaAla 2. An isolated and purified DNA sequence according to claim 1, wherein DNA sequences encoding the subunits α and subunit β are as follows:

Subunit α

```
          10         20         30         40
TCAGTAACGATCGACCACACAACGGAGAACGCCGCACCGG
          50         60         70         80
CCCAGGCGGCGGTCTCCGA CCGGGCGTGGGCACTGTTCCG
          90        100        110        120
CGCACTCGACGGTAAGGGATTGGTACCCGACGGTTACGTC
         130        140        150        160
GAGGGATGGAAGAAGACCTTCGAGGAGGACTTCAGTCCAA
         170        180        190        200
GGCGCGGAGCGGAATTGGTAGCGCGCGCATGGACCGACCC
         210        220        230        240
CGAGTTCCGGCAGCTGCTTCTCACCGACGGTACCGCCGCA
         250        260        270        280
GTTGCCCAGTACGGATACCTGGGCCCCCAGGGCGAATACA
         290        300        310        320
TCGTGGCAGTCGAAGACACCCCGACACTCAAGAACGTGAT
         330        340        350        360
CGTGTGCTCGCTGTGTTCATGCACCGCGTGGCCCATCCTC
         370        380        390        400
GGTCTGCCACCCACCTGGTACAAGAGCTTCGAATACCGTG
         410        420        430        440
CGCGCGTGGTCCGCGAACCACGGAAGGTTCTCTCCGAGAT
         450        460        470        480
GGGAACCGAGATCGCGTCGGACATCGAGATTCGCGTCTAC
         490        500        510        520
GACACCACCGCCGAAACTCGCTACATGGTCCTCCCGCAGC
         530        540        550        560
GTCCCGCCGGCACCGAAGGCTGGAGCCAGGAACAACTGCA
         570        580        590        600
GGAAATCGTCACCAAGGACTGCCTGATCGGGGTTGCAATC
         610
CCGCAGGTTCCCACCGTC
```

Subunit β

```
          10         20         30         40
ATGGATGGAGTACACGATCTTGCCGGAGTACAAGGCTTCG
          50         60         70         80
GCAAAGTCCCGCATACCGTCAACGCCGACATCGGCCCCAC
          90        100        110        120
CTTTCACGCCGAATGGGAACACCTGCCCTACAGCCTGATG
         130        140        150        160
TTCGCCGGTGTCGCCGAACTCGGGGCCTTCAGCGTCGACG
         170        180        190        200
AAGTGCGATACGTCGTCGAGCGGATGGAGCCGCGCCACTA
         210        220        230        240
CATGATGACCCCGTACTACGAGAGGTACGTCATCGGTGTC
```

-continued

```
         250       260       270       280
GCGACATTGATGGTCGAAAAGGGAATCCTGACGCAGGACG
         290       300       310       320
AACTCGAAAGCCTTGCGGGGGGACCGTTCCCACTGTCACG
         330       340       350       360
GCCCAGCGAATCCGAAGGGCGGCCGGCACCCGTCGAGACG
         370       380       390       400
ACCACCTTCGAAGTCGGGCAGCGAGTACGCGTACGCGACG
         410       420       430       440
AGTACGTTCCGGGGCATATTCGAATGCCTGCATACTGCCG
         450       460       470       480
TGGACGAGTGGGAACCATCTCTCATCGAACTACCGAGAAG
         490       500       510       520
TGGCCGTTTCCCGACGCAATCGGCCACGGGCGCAACGACG
         530       540       550       560
CCGGCGAAGAACCGACGTACCACGTGAAGTTCGCCGCCGA
         570       580       590       600
GGAATTGTTCGGTAGCGACACCGACGGTGGAAGCGTCGTT
         610       620       630
GTCGACCTCTTCGAGGGTT ACCTCGAGCCTGCGGCC
```

3. A vector comprising the DNA sequence of claim 1.

4. A vector comprising the DNA sequence of claim 2.

5. The vector according to claim 3 wherein the vector is pYUK121.

6. A procaryotic host cell transformed with the vector of claim 3.

7. A procaryotic host cell transformed with the vector of claim 4.

8. A procaryotic host cell transformed with the vector of claim 4, wherein the host cell is *Escherichia coli*.

9. A procaryotic host cell transformed with the vector of claim 7 wherein the host cell is *Escherichia coli*.

10. A procaryotic host cell transformed with the vector of claim 6 wherein the transformed host cell is JM1051-pYUK121 (FERM BP-1937).

11. A method for producing nitrile hydratase, comprising culturing the transformed host cell of claim 6 in a medium to produce nitrile hydratase and recovering the nitrile hydratase accumulated in the medium.

12. A method for producing nitrile hydratase, comprising culturing the transformed host cell of claim 7 in a medium to produce nitrile hydratase and recovering the nitrile hydratase accumulated in the medium.

* * * * *